(12) United States Patent
Gill et al.

(10) Patent No.: US 11,234,842 B2
(45) Date of Patent: Feb. 1, 2022

(54) SYSTEMS AND METHODS FOR CONTROLLING A PROSTHETIC HAND

(71) Applicant: Touch Bionics Limited, Livingston (GB)

(72) Inventors: Hugh Gill, Strathclyde (GB); Jess Murphy, Powell, OH (US)

(73) Assignee: Touch Bionics Limited, Livingston (GB)

( * ) Notice: Subject to any disclaimer, the term of this patent is extended or adjusted under 35 U.S.C. 154(b) by 275 days.

(21) Appl. No.: 16/249,696

(22) Filed: Jan. 16, 2019

(65) Prior Publication Data

US 2019/0216618 A1 Jul. 18, 2019

Related U.S. Application Data

(63) Continuation of application No. 15/307,385, filed as application No. PCT/GB2015/051356 on May 8, 2015, now Pat. No. 10,265,197.

(30) Foreign Application Priority Data

May 9, 2014 (GB) ...................................... 1408253

(51) Int. Cl.
*A61F 2/70* (2006.01)
*A61F 2/58* (2006.01)
(Continued)

(52) U.S. Cl.
CPC ................ *A61F 2/70* (2013.01); *A61F 2/583* (2013.01); *A61F 2/68* (2013.01); *A61F 2/72* (2013.01);
(Continued)

(58) Field of Classification Search
CPC .... A61F 2/583; A61F 2/68; A61F 2/70; A61F 2/72; A61F 2002/701; A61F 2002/704;
(Continued)

(56) References Cited

U.S. PATENT DOCUMENTS

| 1,507,682 A | 9/1924 | Pecorella et al. |
| 2,445,711 A | 7/1948 | Fitch |
| (Continued) | | |

FOREIGN PATENT DOCUMENTS

| CN | 1803413 | 7/2006 |
| DE | 309 367 | 11/1918 |
| (Continued) | | |

OTHER PUBLICATIONS

Dspic microcontrollers introduction and features. STmicroelectronics (Year: 2013).*

(Continued)

*Primary Examiner* — Christie L Bahena
(74) *Attorney, Agent, or Firm* — Knobbe, Martens, Olson & Bear, LLP

(57) ABSTRACT

A method of controlling a prosthetic hand having at least one motorized component is provided. The method comprises the steps of providing the hand with a first wireless transceiver and a controller in communication with one another, storing at least one manipulation instruction relating to the at least one component, and assigning a code relating to the at least one manipulation instruction to at least one second wireless transceiver. The at least one second transceiver is placed in a location at which the at least one manipulation instruction is to be given, and the controller manipulates the at least one component in accordance with the at least one manipulation instruction when the first transceiver communicates to the controller that the at least one second transceiver is within a predetermined distance of the first transceiver. Related methods and systems for controlling a prosthetic hand are also provided.

12 Claims, 6 Drawing Sheets

(51) Int. Cl.
*A61F 2/72* (2006.01)
*A61F 2/68* (2006.01)
*H04W 4/80* (2018.01)
*A61F 2/76* (2006.01)

(52) U.S. Cl.
CPC ... *A61F 2002/701* (2013.01); *A61F 2002/704* (2013.01); *A61F 2002/705* (2013.01); *A61F 2002/707* (2013.01); *A61F 2002/765* (2013.01); *A61F 2002/7615* (2013.01); *H04W 4/80* (2018.02)

(58) Field of Classification Search
CPC .......... A61F 2002/705; A61F 2002/707; A61F 2002/7615; A61F 2002/765; H04W 4/80
See application file for complete search history.

(56) References Cited

U.S. PATENT DOCUMENTS

| | | |
|---|---|---|
| 2,477,463 A | 7/1949 | Otterman |
| 2,482,555 A | 9/1949 | Otterman |
| 2,508,156 A | 5/1950 | Gillman |
| 2,516,791 A | 7/1950 | Motis et al. |
| 2,592,842 A | 4/1952 | Alderson |
| 2,669,727 A | 2/1954 | Opuszenski |
| 2,983,162 A | 5/1961 | Musser |
| 3,406,584 A | 10/1968 | Roantree |
| 3,509,583 A | 5/1970 | Fraloli |
| 3,683,423 A | 8/1972 | Crapanzano |
| 3,751,995 A | 8/1973 | Carlson |
| 3,837,010 A | 9/1974 | Prout |
| 3,866,246 A | 2/1975 | Seamone et al. |
| 3,883,900 A | 5/1975 | Jerard et al. |
| 3,922,930 A | 12/1975 | Fletcher et al. |
| 4,030,141 A | 6/1977 | Graupe |
| 4,044,274 A | 8/1977 | Ohm |
| 4,114,464 A | 9/1978 | Schubert et al. |
| 4,197,592 A | 4/1980 | Klein |
| 4,398,110 A | 8/1983 | Flinchbaugh et al. |
| 4,558,704 A | 12/1985 | Petrofsky |
| 4,577,127 A | 3/1986 | Ferree et al. |
| 4,623,354 A | 11/1986 | Childress et al. |
| 4,678,952 A | 7/1987 | Peterson et al. |
| 4,808,187 A | 2/1989 | Patterson et al. |
| 4,813,303 A | 3/1989 | Beezer et al. |
| 4,822,238 A | 4/1989 | Kwech |
| 4,955,918 A | 9/1990 | Lee |
| 4,960,425 A | 10/1990 | Yan et al. |
| 4,990,162 A | 2/1991 | LeBlanc et al. |
| 5,020,162 A | 6/1991 | Kersten et al. |
| 5,062,673 A | 11/1991 | Mimura |
| 5,088,125 A | 2/1992 | Ansell et al. |
| 5,133,776 A | 7/1992 | Chen |
| 5,246,463 A | 9/1993 | Giampapa |
| 5,252,102 A | 10/1993 | Singer et al. |
| 5,387,245 A | 2/1995 | Fay et al. |
| 5,413,611 A | 5/1995 | Haslam, II et al. |
| 5,498,472 A | 3/1996 | Gold |
| 5,581,166 A | 12/1996 | Eismann et al. |
| 5,785,960 A | 7/1998 | Rigg et al. |
| 5,851,194 A | 12/1998 | Fratrick |
| 5,852,675 A | 12/1998 | Matsuo et al. |
| 5,888,213 A | 3/1999 | Sears et al. |
| 5,888,246 A | 3/1999 | Gow |
| 6,111,973 A | 8/2000 | Holt et al. |
| 6,175,962 B1 | 1/2001 | Michelson |
| 6,223,615 B1 | 5/2001 | Huck |
| 6,244,873 B1 | 6/2001 | Hill et al. |
| 6,344,062 B1 | 2/2002 | Abboudi et al. |
| 6,361,570 B1 | 3/2002 | Gow |
| 6,494,662 B1 | 12/2002 | De Montalembert |
| 6,589,287 B2 | 7/2003 | Lundborg |
| 6,660,042 B1 | 12/2003 | Curcie et al. |
| 6,660,043 B2 | 12/2003 | Kajitani et al. |
| 6,684,754 B2 | 2/2004 | Comer |
| 6,786,112 B2 | 9/2004 | Ruttor |
| 7,056,297 B2 | 6/2006 | Dohno et al. |
| 7,144,430 B2 | 12/2006 | Archer et al. |
| 7,243,569 B2 | 7/2007 | Takahashi et al. |
| 7,316,304 B2 | 1/2008 | Heravi et al. |
| 7,316,795 B1 | 1/2008 | Knauss |
| 7,370,896 B2 | 5/2008 | Anderson et al. |
| 7,373,721 B2 | 5/2008 | Bergamasco et al. |
| 7,640,680 B1 | 1/2010 | Castro |
| 7,823,475 B2 | 11/2010 | Hirabayashi et al. |
| 7,828,857 B2 | 11/2010 | Farnsworth et al. |
| 7,867,287 B2 | 1/2011 | Puchhammer |
| 7,922,773 B1 | 4/2011 | Kuiken |
| 8,016,893 B2 | 9/2011 | Weinberg et al. |
| 8,100,986 B2 | 1/2012 | Puchhammer et al. |
| 8,197,554 B2 | 6/2012 | Whiteley et al. |
| 8,257,446 B2 | 9/2012 | Puchhammer |
| 8,337,568 B2 | 12/2012 | Macduff |
| 8,396,546 B2 | 3/2013 | Hirata et al. |
| 8,491,666 B2 | 7/2013 | Schulz |
| 8,579,991 B2 | 11/2013 | Puchhammer |
| 8,593,255 B2 | 11/2013 | Pang et al. |
| 8,657,887 B2 | 2/2014 | Gill |
| 8,662,552 B2 | 3/2014 | Torres-Jara |
| 8,663,339 B2 | 3/2014 | Inschlag et al. |
| 8,690,963 B2 | 4/2014 | Puchhammer |
| 8,696,763 B2 | 4/2014 | Gill |
| 8,808,397 B2 | 8/2014 | Gow |
| 8,821,587 B2 | 9/2014 | Lanier et al. |
| 8,828,096 B2 | 9/2014 | Gill |
| 8,840,680 B2 | 9/2014 | Goldfarb et al. |
| 8,986,395 B2 | 3/2015 | McLeary |
| 8,995,760 B2 | 3/2015 | Gili |
| 9,034,055 B2 | 5/2015 | Vinjamuri et al. |
| 9,114,030 B2 | 8/2015 | van der Merwe et al. |
| 9,121,699 B2 | 9/2015 | van der Merwe et al. |
| 9,174,339 B2 | 11/2015 | Goldfarb et al. |
| 9,265,625 B2 | 2/2016 | Goldfarb et al. |
| 9,278,012 B2 | 3/2016 | Gill |
| 9,387,095 B2 | 7/2016 | McLeary et al. |
| 9,402,749 B2 | 8/2016 | Gill et al. |
| 9,463,100 B2 | 10/2016 | Gill |
| 9,720,515 B2 | 8/2017 | Wagner et al. |
| 9,730,815 B2 | 8/2017 | Goldfarb et al. |
| 9,826,933 B2 | 11/2017 | van der Merwe et al. |
| 9,839,534 B2 | 12/2017 | Lipsey et al. |
| 9,901,465 B2 | 2/2018 | Lanier, Jr. et al. |
| 9,931,230 B2 | 4/2018 | Sikdar et al. |
| 9,999,522 B2 | 6/2018 | Gill |
| 10,265,197 B2 | 4/2019 | Gill et al. |
| 10,318,863 B2 | 8/2019 | Lock et al. |
| 10,369,024 B2 | 8/2019 | Gill |
| 10,398,576 B2 | 9/2019 | Gill et al. |
| 10,610,385 B2 | 4/2020 | Meijer et al. |
| 2001/0023058 A1 | 9/2001 | Jung et al. |
| 2002/0016631 A1 | 2/2002 | Marchitto et al. |
| 2002/0135241 A1 | 9/2002 | Kobayashi et al. |
| 2003/0036805 A1 | 2/2003 | Senior |
| 2004/0002672 A1 | 1/2004 | Carlson |
| 2004/0078299 A1 | 4/2004 | Down-Logan et al. |
| 2004/0103740 A1 | 6/2004 | Townsend et al. |
| 2004/0181289 A1 | 9/2004 | Bedard et al. |
| 2004/0182125 A1 | 9/2004 | McLean |
| 2005/0021154 A1 | 1/2005 | Brimalm |
| 2005/0021155 A1 | 1/2005 | Brimalm |
| 2005/0093997 A1 | 5/2005 | Dalton et al. |
| 2005/0101693 A1 | 5/2005 | Arbogast et al. |
| 2005/0192677 A1 | 9/2005 | Ragnarsdottir et al. |
| 2006/0029909 A1 | 2/2006 | Kaczkowski |
| 2006/0054782 A1 | 3/2006 | Olsen et al. |
| 2006/0158146 A1 | 7/2006 | Tadano |
| 2006/0167564 A1 | 7/2006 | Flaherty et al. |
| 2006/0212129 A1 | 9/2006 | Lake et al. |
| 2006/0229755 A1 | 10/2006 | Kuiken et al. |
| 2006/0251408 A1 | 11/2006 | Konno et al. |
| 2007/0032884 A1 | 2/2007 | Veatch |
| 2007/0058860 A1 | 3/2007 | Harville et al. |
| 2007/0061111 A1 | 3/2007 | Jung et al. |

(56) References Cited

U.S. PATENT DOCUMENTS

| | | |
|---|---|---|
| 2007/0071314 A1 | 3/2007 | Bhatti et al. |
| 2007/0230832 A1 | 10/2007 | Usui et al. |
| 2007/0260328 A1 | 11/2007 | Bertels et al. |
| 2008/0058668 A1 | 3/2008 | Seyed Momen et al. |
| 2008/0146981 A1 | 6/2008 | Greenwald et al. |
| 2008/0215162 A1 | 9/2008 | Farnsworth et al. |
| 2008/0260218 A1 | 10/2008 | Smith et al. |
| 2008/0262634 A1 | 10/2008 | Puchhammer |
| 2009/0213379 A1 | 8/2009 | Carroll et al. |
| 2010/0016990 A1 | 1/2010 | Kurtz |
| 2010/0116078 A1 | 5/2010 | Kim |
| 2010/0271177 A1 | 10/2010 | Pang et al. |
| 2010/0274365 A1 | 10/2010 | Evans et al. |
| 2010/0328049 A1* | 12/2010 | Frysz .................. G08B 13/248 340/10.51 |
| 2011/0136376 A1 | 6/2011 | Johnson et al. |
| 2011/0203027 A1 | 8/2011 | Flather et al. |
| 2011/0237381 A1 | 9/2011 | Puchhammer |
| 2011/0257765 A1 | 10/2011 | Evans et al. |
| 2011/0264238 A1 | 10/2011 | van der Merwe et al. |
| 2011/0265597 A1 | 11/2011 | Long |
| 2011/0278061 A1 | 11/2011 | Farnan |
| 2012/0004884 A1 | 1/2012 | Fillol et al. |
| 2012/0014571 A1 | 1/2012 | Wong et al. |
| 2012/0061155 A1 | 3/2012 | Berger et al. |
| 2012/0099788 A1 | 4/2012 | Bhatti et al. |
| 2012/0109337 A1 | 5/2012 | Schulz |
| 2012/0123558 A1 | 5/2012 | Gill |
| 2012/0204665 A1 | 8/2012 | Baudasse |
| 2012/0280812 A1 | 11/2012 | Sheikman et al. |
| 2012/0286629 A1 | 11/2012 | Johnson et al. |
| 2012/0303136 A1 | 11/2012 | Macduff |
| 2012/0330439 A1 | 12/2012 | Goldfarb et al. |
| 2013/0041476 A1 | 2/2013 | Schulz |
| 2013/0053984 A1 | 2/2013 | Hunter et al. |
| 2013/0076699 A1 | 3/2013 | Spencer |
| 2013/0144197 A1 | 6/2013 | Ingimundarson et al. |
| 2013/0253705 A1 | 9/2013 | Goldfarb et al. |
| 2013/0268094 A1 | 10/2013 | Van Wiemeersch |
| 2014/0236314 A1 | 8/2014 | Van Wiemeersch |
| 2014/0324189 A1 | 10/2014 | Gill et al. |
| 2014/0371871 A1 | 12/2014 | Farina et al. |
| 2015/0142082 A1 | 5/2015 | Simon et al. |
| 2015/0216681 A1 | 8/2015 | Lipsey et al. |
| 2015/0328019 A1* | 11/2015 | Park .................. A61F 2/54 623/24 |
| 2015/0351935 A1 | 12/2015 | Donati et al. |
| 2015/0374515 A1 | 12/2015 | Meijer et al. |
| 2016/0120664 A1 | 5/2016 | Schultz |
| 2016/0143751 A1 | 5/2016 | Chestek et al. |
| 2016/0166409 A1 | 6/2016 | Goldfarb et al. |
| 2016/0287422 A1 | 10/2016 | Kelly et al. |
| 2017/0007424 A1 | 1/2017 | Gill |
| 2017/0049583 A1 | 2/2017 | Belter et al. |
| 2017/0049586 A1 | 2/2017 | Gill et al. |
| 2017/0209288 A1 | 7/2017 | Veatch |
| 2017/0281368 A1 | 10/2017 | Gill |
| 2017/0340459 A1 | 11/2017 | Mandelbaum |
| 2018/0014744 A1 | 1/2018 | Duerstock et al. |
| 2018/0064563 A1 | 3/2018 | Gill |
| 2018/0071115 A1 | 3/2018 | Lipsey et al. |
| 2018/0116829 A1 | 5/2018 | Gaston et al. |
| 2018/0168477 A1 | 6/2018 | Graimann et al. |
| 2018/0221177 A1 | 8/2018 | Kaltenbach et al. |
| 2018/0235782 A1 | 8/2018 | Choi et al. |
| 2018/0256365 A1 | 9/2018 | Bai |
| 2018/0296368 A1 | 10/2018 | Gill |
| 2019/0091040 A1 | 3/2019 | Gill |
| 2020/0054466 A1 | 2/2020 | Gill et al. |
| 2020/0197193 A1 | 6/2020 | Byrne et al. |
| 2020/0268532 A1 | 8/2020 | Meijer et al. |

FOREIGN PATENT DOCUMENTS

| | | |
|---|---|---|
| DE | 24 34 834 | 2/1976 |
| DE | 198 54 762 | 6/2000 |
| DE | 101 05 814 | 9/2002 |
| DE | 203 15 575 | 1/2004 |
| DE | 10 2012 009 699 | 11/2013 |
| EP | 0 145 504 | 6/1985 |
| EP | 0 219 478 | 4/1987 |
| EP | 0 256 643 | 2/1988 |
| EP | 0 484 173 | 5/1992 |
| EP | 0 947 899 | 10/1999 |
| EP | 0 968 695 | 1/2000 |
| EP | 1 043 003 | 10/2000 |
| EP | 1 617 103 | 1/2006 |
| EP | 2 532 927 | 12/2012 |
| EP | 2 612 619 | 7/2013 |
| EP | 2 114 316 | 7/2014 |
| EP | 2 125 091 | 4/2016 |
| EP | 2 467 101 | 4/2016 |
| EP | 2 696 814 | 1/2017 |
| GB | 326 970 | 3/1930 |
| GB | 607 001 | 2/1947 |
| GB | 1 386 942 | 3/1975 |
| GB | 1 510 298 | 5/1978 |
| GB | 1 585 256 | 2/1981 |
| GB | 2 067 074 | 7/1981 |
| GB | 2 146 406 | 4/1985 |
| GB | 2 357 725 A | 7/2001 |
| GB | 2 444 679 | 6/2008 |
| JP | 53-011456 | 2/1978 |
| JP | 53-094633 | 8/1978 |
| JP | 07-174631 | 7/1995 |
| JP | 2001-082913 | 3/2001 |
| JP | 2001-299448 | 10/2001 |
| JP | 2002-131135 | 5/2002 |
| JP | 2002-310242 | 10/2002 |
| JP | 2003-134526 | 5/2003 |
| JP | 2004-073802 | 3/2004 |
| JP | 2004-224280 | 8/2004 |
| WO | WO 95/024875 | 9/1995 |
| WO | WO 96/023643 | 8/1996 |
| WO | WO 00/025840 | 5/2000 |
| WO | WO 00/069375 | 11/2000 |
| WO | WO 01/004838 | 1/2001 |
| WO | WO 02/049534 | 6/2002 |
| WO | WO 03/017877 | 3/2003 |
| WO | WO 03/017878 | 3/2003 |
| WO | WO 03/017880 | 3/2003 |
| WO | WO 2006/058190 | 6/2006 |
| WO | WO 2006/069264 | 6/2006 |
| WO | WO 2006/078432 | 7/2006 |
| WO | WO 2006/086504 | 8/2006 |
| WO | WO 2006/092604 | 9/2006 |
| WO | WO 2006/110790 | 10/2006 |
| WO | WO 2007/063266 | 6/2007 |
| WO | WO 2007/076764 | 7/2007 |
| WO | WO 2007/076765 | 7/2007 |
| WO | WO 2007/126854 | 11/2007 |
| WO | WO 2007/127973 | 11/2007 |
| WO | WO 2008/044052 | 4/2008 |
| WO | WO 2008/044207 | 4/2008 |
| WO | WO 2008/092695 | 8/2008 |
| WO | WO 2008/098059 | 8/2008 |
| WO | WO 2008/098072 | 8/2008 |
| WO | WO 2009/011682 | 1/2009 |
| WO | WO 2010/018358 | 2/2010 |
| WO | WO 2010/051798 | 5/2010 |
| WO | WO 2010/149967 | 12/2010 |
| WO | WO 2011/001136 | 1/2011 |
| WO | WO 2011/022569 | 2/2011 |
| WO | WO 2011/036473 | 3/2011 |
| WO | WO 2011/036626 | 3/2011 |
| WO | WO 2011/088964 | 7/2011 |
| WO | WO 2011/107778 | 9/2011 |
| WO | WO 2011/143004 | 11/2011 |
| WO | WO 2014/111843 | 7/2014 |
| WO | WO 2015/120076 | 8/2015 |
| WO | WO 2015/120083 | 8/2015 |

(56) References Cited

FOREIGN PATENT DOCUMENTS

| WO | WO 2016/051138 | 4/2016 |
|---|---|---|
| WO | WO 2017/137930 | 8/2017 |
| WO | WO 2018/054945 | 3/2018 |
| WO | WO 2018/132711 | 7/2018 |
| WO | WO 2018/178420 | 10/2018 |
| WO | WO 2018/218129 | 11/2018 |

OTHER PUBLICATIONS

Kim, Tae Sung. Development of an Anthromorphic Prosthetic Hand H3 and its Control. (Year: 2008).*
Albu-Schaffer et al., "Soft Robotics", IEEE Robotics & Automation Magazine, Sep. 2008, vol. 15, No. 3, pp. 20-30.
Antonio et al., "A Virtual Upper Limb Prosthesis as a Training System", 7th International Conference on Electrical Engineering, Computing Science and Automatic Control (CCE 2010) Tuxtla Gutiérrez, Chiapas, México. Sep. 8-10, 2010, pp. 210-215.
Bellman et al., "SPARKy 3: Design of an Active Robotic Ankle Prosthesis with two Actuated Degrees of Freedom Using Regenerative Kinetics", in Proceedings of the 2nd Biennial IEEE/RAS-EMBS International Conference on Biomedical Robotics and Biomechatronics, Oct. 19-22, 2008, Scottsdale. AZ, pp. 511-516.
Belter et al., "Mechanical Design and Performance Specifications or Anthropomorphic Prosthetic Hands: A Review", JRRD, Jan. 2013, vol. 50, No. 5, pp. 599-618.
Biddiss et al., "Consumer Design Priorities for Upper Limb Prosthetics", Disability and Rehabilitation: Assistive Technology, Nov. 2007, vol. 2, No. 6, pp. 346-357.
Biddiss et al., "Upper Limb Prosthesis Use and Abandonment: A Survey of the Last 25 Years", Prosthetics and Orthotics International, Sep. 2007, vol. 31, No. 3, pp. 236-257.
Biddiss et al., "Upper-Limb Prosthetics: Critical Factors in Device Abandonment", American Journal of Physical Medicine & Rehabilitation, Dec. 2007, vol. 86, No. 12, pp. 977-987.
Chicoine et al., "Prosthesis-Guided Training of Pattern Recognition-Controlled Myoelectric Prosthesis", in Proceedings of the 34th Annual International Conference of the IEEE EMBS, San Diego, CA, Aug. 28-Sep. 1, 2012, pp. 1876-1879.
Childress et al., "Control of Limb Prostheses", American Academy of Orthopaedic Surgeons, Chapter 12, pp. 173-195, 2004.
Choi et al., "Design of High Power Permanent Magnet Motor with Segment Rectangular Copper Wire and Closed Slot Opening on Electric Vehicles", IEEE Transactions on Magnetics, Jun. 2010, vol. 46. No. 9, pp. 2070-2073.
Cipriani et al., "On the Shared Control of an EMG-Controlled Prosthetic Hand: Analysis of User-Prosthesis Interaction", IEEE Transactions on Robotics, Feb. 2008, vol. 24, No. 1, pp. 170-184.
Connolly, "Prosthetic Hands from Touch Bionics", Industrial Robot, Emerald Group Publishing Limited, 2008, vol. 35, No. 4, pp. 290-293.
Controzzi et al., "Miniaturized Non-Back-Drivable Mechanism for Robotic Applications", Mechanism and Machine Theory, Oct. 2010, vol. 45, No. 10, pp. 1395-1406.
Damian et al., "Artificial Tactile Sensing of Position and Slip Speed by Exploiting Geometrical Features", IEEE/ASME Transactions on Mechatronics, Feb. 2015, vol. 20, No. 1, pp. 263-274.
"DC Circuit Theory", https://www.electronics-tutorials.ws/dccircuits/dcp_1.html, Date verified by the Wayback Machine Apr. 23, 2013, pp. 16.
Dechev et al., "Multiple Finger, Passive Adaptive Grasp Prosthetic Hand", Mechanism and Machine Theory, Oct. 1, 2001, vol. 36, No. 10, pp. 1157-1173.
Dellorto, Danielle, "Bionic Hands Controlled by iPhone App", CNN, Apr. 12, 2013, pp. 4 http://www.cnn.com/2013/04/12/health/bionic-hands.
"DuPont Engineering Design—The Review of DuPont Engineering Polymers in Action", http://www.engpolymer.co.kr/x_data/magazine/engdesign07_2e.pdf, 2007, pp. 16.

Engeberg et al., "Adaptive Sliding Mode Control for Prosthetic Hands to Simultaneously Prevent Slip and Minimize Deformation of Grasped Objects," IEEE/ASME Transactions on Mechatronics, Feb. 2013, vol. 18, No. 1, pp. 376-385.
Fougner et al., "Control of Upper Limb Prostheses: Terminology and Proportional Myoelectric Control-A Review", IEEE Transactions on Neural Systems Rehabilitation Engineering, Sep. 2012, vol. 20. No. 5, pp. 663-677.
Fukuda et al., "Training of Grasping Motion Using a Virtual Prosthetic Control System", 2010 IEEE International Conference on Systems Man and Cybernetics (SMC), Oct. 10-13, 2010, pp. 1793-1798.
Gaine et al., "Upper Limb Traumatic Amputees. Review of Prosthetic Use", The Journal of Hand Surgery, Feb. 1997, vol. 22B, No. 1, pp. 73-76.
Grip Chips™, Datasheet, May 15, 2014, Issue 1, http://touchbionics.com/sites/default/files/files/Grip%20Chip%20datasheet%20May%202014.pdf. pp. 1.
Heckathorne, Craig W., "Components for Electric-Powered Systems", American Academy of Orthopaedic Surgeons, Chapter 11, pp. 145-171, 2004.
Hojjat et al., "A Comprehensive Study on Capabilities and Limitations of Roller-Screw with Emphasis on Slip Tendency", Mechanism and Machine Theory, 2009, vol. 44, No. 10, pp. 1887-1899.
Hsieh, Chiu-Fan., "Dynamics Analysis of Cycloidal Speed Reducers with Pinwheel and Nonpinwheel Designs", ASME Journal of Mechanical Design, Sep. 2014, vol. 136, No. 9, pp. 091008-1-091008-11.
International Preliminary Report on Patentability and Written Opinion in Application No. PCT/GB2015/051356, dated Nov. 15, 2016.
International Search Report and Written Opinion in Application No. PCT/GB2015/051356, dated Jul. 14, 2015.
Jebsen et al., "An Objective and Standardized Test of Hand Function", Archives of Physical Medicine and Rehabilitation, Jun. 1969, vol. 50, No. 6, pp. 311-319.
Johannes et al., "An Overview of the Developmental Process for the Modular Prosthetic Limb," John Hopkins APL Technical Digest, 2011, vol. 30, No. 3, pp. 207-216.
Kent et al., "Electromyogram Synergy Control of a Dexterous Artificial Hand to Unscrew and Screw Objects", Journal of Neuroengineering and Rehabilitation, 2014, vol. 11, No. 1, pp. 1-20.
Kermani et al., "Friction Identification and Compensation in Robotic Manipulators", IEEE Transactions on Instrumentation and Measurement, Dec. 2007, vol. 56, No. 6, pp. 2346-2353.
Kuiken et al., "Targeted Muscle Reinnervation for Real-Time Myoelectric Control of Multifunction Artificial Arms", JAMA, Feb. 11, 2009, vol. 301, No. 6, pp. 619-628.
Kyberd et al., "Two-Degree-of-Freedom Powered Prosthetic Wrist", Journal of Rehabilitation Research & Development, 2011, vol. 48, No. 6, pp. 609-617.
Lamounier et al., "On the Use of Virtual and Augmented Reality for Upper Limb Prostheses Training and Simulation", 2010 Annual International Conference of the IEEE Engineering in Medicine and Biology Society (EMBC), Aug. 31-Sep. 4, 2010, pp. 2451-2454.
Light et al., "Establishing a Standardized Clinical Assessment Tool of Pathologic and Prosthetic Hand Function: Normative Data, Reliability, and Validity", Archives of Physical Medicine and Rehabilitation, Jun. 2002, vol. 83, pp. 776-783.
Mace et al., "Augmenting Neuroprosthetic Hand Control Through Evaluation of a Bioacoustic interface", IEEE/RSJ International Conference on Intelligent Robots and Systems (IROS), Tokyo, Japan, Nov. 3-7, 2013, pp. 7.
Majd et al., "A Continuous Friction Model for Servo Systems with Stiction", in Proceedings of the IEEE Conference on Control Applications, 1995, pp. 296-301.
Martinez-Villalpando et al., "Agonist-Antagonist Active Knee Prosthesis: A Preliminary Study in Level-Ground Walking", Journal of Rehabilitation Research & Development, vol. 46, No. 3, 2009, pp. 361-374.
Maxon Precision Motors, Inc., "Maxon Flat Motor: EX 10 flat 10 mm, brushless, 0.25 Watt", Specification, May 2011, p. 181.
Maxon Precision Motors, Inc., "Maxon EC Motor: EC10 10 mm, brushless, 8 Watt", Specification, May 2011, p. 140.

(56) References Cited

OTHER PUBLICATIONS

Miller et al., "Summary and Recommendations of the Academy's State of the Science Conference on Upper Limb Prosthetic Outcome Measures", Journal of Prosthetics Orthotics, 2009, vol. 21, pp. 83-89.

Montagnani et al., "Is it Finger or Wrist Dexterity that is Missing in Current Hand Prostheses?", IEEE Transactions on Neural Systems and Rehabilitation Engineering, Jul. 2015, vol. 23, No. 4, pp. 600-609.

Morita et al., "Development of 4-D.O.F. Manipulator Using Mechanical Impedance Adjuster", Proceedings of the 1996 IEEE International Conference on Robotics and Automation, Minneapolis, MN, Apr. 1996, pp. 2902-2907.

Ninu et al., "Closed-Loop Control of Grasping with a Myoelectric Hand Prosthesis: Which are the Relevant Feedback Variable for Force Control?" IEEE Transactions on Neural Systems and Rehabilitation Engineering, Sep. 2014, vol. 22, No. 5, pp. 1041-1052.

Osborn et al., "Utilizing Tactile Feedback for Biomimetic Grasping Control in Upper Limb Prostheses". Department of Biomedical Engineering, Johns Hopkins University, Baltimore, USA, 2013, pp. 4.

Pedrocchi et al., "MUNDUS Project: Multimodal Neuroprosthesis for Daily Upper Limb Support", Journal of Neuroengineering and Rehabilitation, 2013, vol. 10, No. 66, pp. 20. http://www.jneuroengrehab.com/content/10/1/66.

Pinzur et al., "Functional Outcome Following Traumatic Upper Limb Amputation and Prosthetic Limb Fitting", J. Hand Surgery, Amer. Vol., 1994. vol. 19, pp. 836-839.

Press Release, "Touch Bionics Introduce Digitally Controlled Supro Wrist", http://www.touchbionics.com/news-events/news/touch-bionics-introduce-digitally-controlled-supro-wrist, May 3, 2016 in 2 pages.

Raspopovic et al., "Restoring Natural Sensory Feedback in Real-Time Bidirectional Hand Prostheses", Science Translational Medicine, Feb. 5, 2014, vol. 6, No. 222, pp. 1-10.

Resnik et al., "The DEKA Arm: Its Features, Functionality, and Evolution During the Veterans Affairs Study to Optimize the DEKA Arm", Prosthetics and Orthotics International, 2014, vol. 38, No. 6, pp. 492-504.

Scheme et al., "Electromyogram Pattern Recognition for Control of Powered Upper-Limb Prostheses: State of the Art and Challenges for Clinical Use", Journal of Rehabilitation Research & Development (JRRD), 2011, vol. 48, No. 6, pp. 643-659.

Scheme et al., "Motion Normalized Proportional Control for Improved Pattern Recognition-Based Myoelectric Control", IEEE Transactions on Neural Systems and Rehabilitation Engineering, Jan. 2014, vol. 22, No. 1, pp. 149-157.

Sensinger et al., "Cycloid vs. Harmonic Drives for use in High Ratio, Single Stage Robotic Transmissions", 2012 IEEE Conference on Robotics and Automation (ICRA), Saint Paul, MN, USA, May 14-18, 2012, pp. 4130-4135.

Sensinger, "Efficiency of High-Sensitivity Gear Trains, such as Cycloid Drives", Journal of Mechanical Design, Jul. 2013, vol. 135, No. 7, pp. 071006-1-071006-9.

Sensinger et al., "Exterior vs. Interior Rotors in Robotic Brushless Motors", 2011 IEEE International Conference on Robotics and Automation (ICRA), Shanghai, China, May 9-13, 2011, pp. 2764-2770.

Sensinger, "Selecting Motors for Robots Using Biomimetic Trajectories: Optimum Benchmarks, Windings, and other Considerations," 2010 IEEE International Conference on Robotics and Automation (ICRA), Anchorage, AL, USA, May 3-8, 2010, pp. 4175-4181.

Sensinger. "Unified Approach to Cycloid Drive Profile, Stress, and Efficiency Optimization", Journal of Mechanical Design, Feb. 2010, vol. 132, pp. 024503-1-024503-5.

Sensinger et al., "User-Modulated Impedance Control of a Prosthetic Elbow in Unconstrained, Perturbed Motion", IEEE Transactions on Biomedical Engineering, Mar. 2008, vol. 55, No. 3, pp. 1043-1055.

Stix, Gary, "Phantom Touch: Imbuing a Prosthesis with Manual Dexterity", Scientific American, Oct. 1998, pp. 41 & 44.

"Supro Wrist", Touch Bionics, https://web.archive.org/web/20160928141440/http://www.touchbionics.com/products/supro-wrist as archived Sep. 28, 2016 in 3 pages.

Sutton et al., "Towards a Universal Coupler Design for Modern Powered Prostheses", MEC 11 Raising the Standard, Proceedings of the 2011 MyoElectric Controls/Powered Prosthetics Symposium Frederiction, New Brunswick, Canada, Aug. 14-19, 2011, pp. 5.

Tan et al., "A Neural Interface Provides Long-Term Stable Natural Touch Perception", Science Translational Medicine, Oct. 8, 2014, vol. 6, No. 257, pp. 1-11.

Tang, "General Concepts of Wrist Biomechanics and a View from Other Species", The Journal of Hand Surgery, European Volume, Aug. 2008, vol. 33, No. 4, pp. 519-525.

Toledo et al., "A Comparison of Direct and Pattern Recognition Control for a Two Degree-of-Freedom Above Elbow Virtual Prosthesis", in Proceedings 34th Annual International Conference of the IEEE EMBS, 2012, pp. 4332-4335.

"Touch Bionics Grip Chips Let Hand Prostheses Think for Themselves", May 15, 2014, www.medgadget.com/2014/05/touch-blonics-grip-chips-let-hand-prostheses-think-for-themselves.html, pp. 2.

Trachtenberg et al., "Radio Frequency Identification, An Innovative Solution to Guide Dexterous Prosthetic Hands", 33rd Annual International Conference of the IEEE EMBS, Boston, MA, Aug. 30-Sep. 3, 2011, pp. 4.

Vilarino, Martin, "A Novel Wireless Controller for Switching among Modes for an Upper-Limb Prosthesis", The Academy Today, Jan. 2014, vol. 10, No. 1, pp. A-12 to A-15.

Weir et al., "Design of Artificial Arms and Hands for Prosthetic Applications", Biomedical Engineering and Design Handbook, 2009, vol. 2, pp. 537-598.

Wettels et al., "Grip Control Using Biomimetic Tactile Sensing Systems", IEEE/ASME Transactions on Mechatronics, Dec. 2009, vol. 14, No. 6, pp. 718-723.

Whiteside et al., "Practice Analysis Task Force: Practice Analysis of the Disciplines of Orthotics and Prosthetics", American Board for Certification in Orthotics and Prosthetics, Inc., 2000, pp. 1-51.

Wilson et al., "A Bus-Based Smart Myoelectric Electrode/Amplifier-System Requirements", IEEE Transactions on Instrumentation and Measurement, Oct. 2011, vol. 60, No. 10, pp. 3290-3299.

Zampagni et al., "A Protocol for Clinical Evaluation of the Carrying Angle of the Elbow by Anatomic Landmarks", Journal of Shoulder and Elbow Surgery, 2008, vol. 17, No. 1, pp. 106-112.

Baek et al., "Design and Control of a Robotic Finger for Prosthetic Hands", Proceedings of the 1999 IEEE International Conference on Intelligent Robots and Systems, pp. 113-117.

Butterfaß et al., "DLR-Hand II: Next Generation of a Dextrous Robot Hand", IEEE International Conference on Robotics and Automation, Seoul, Korea, May 21-26, 2001, vol. 1, pp. 109-114.

Cotton et al., "Control Strategies for a Multiple Degree of Freedom Prosthetic Hand", Measurement + Control, Feb. 2007, vol. 40, No. 1, pp. 24-27.

Edsinger-Gonzales, Aaron, "Design of a Compliant and Force Sensing Hand for a Humanoid Robot", 2005, pp. 5.

Fildes, Jonathan, "Bionic Hand Wins Top Tech Prize", BBC News, Jun. 9, 2008, http://news.bbc.co.uk/2/hi/science/nature/7443866.stm, pp. 3.

Gaiser et al., "A New Anthropomorphic Robotic Hand", 2008 8th IEEE-RAS International Conference on Humanoid Robots, Dec. 1-3, 2008, Daejeon, Korea, pp. 418-422.

"iLimb Bionic Hand Now Ready for Market", Technovelgy.com, www.technovelgy.com/ct/Science-Fiction-News.asp?NewsNum=1125, as printed Jul. 6, 2020 in 3 pages.

Kargov et al., "Applications of a Fluidic Artificial Hand in the Field of Rehabilitation", Rehabilitation Robotics, Ch. 15, Aug. 2007, pp. 261-286.

Kargov et al., "Development of a Multifunctional Cosmetic Prosthetic Hand", Proceedings for the 2007 IEEE 10th International Conference on Rehabilitation Robotics, Jun. 12-15, 2007, Noordwijk, The Netherlands, pp. 550-553.

Kargov et al., "Modularly Designed Lightweight Anthropomorphic Robot Hand", 2006 IEEE International Conference on Multisensor

(56) References Cited

OTHER PUBLICATIONS

Fusion and Integration for Intelligent Systems, Sep. 3-6, 2006, Heidelberg, Germany, pp. 155-159.
Kawasaki et al., "Design and Control of Five-Fingered Haptic Interface Opposite to Human Hand", IEEE Transactions on Robotics, Oct. 2007, vol. 23, No. 5., pp. 909-918.
Lotti et al., "UBH 3: A Biologically Inspired Robotic Hand", Jan. 2004, pp. 7.
MEC '05: Integrating Prosthetics and Medicine, University of New Brunswick's MyoElectric Controls/Powered Prosthetics Symposium, Aug. 17-19, 2005, Fredericton NB Canada, pp. 260.
Poppe, Zytel HTN Provides a Helping Hand, DuPont Engineering Design 8 (2007), pp. 3.
Puig et al., "A Methodology for the Design of Robotic Hands with Multiple Fingers", International Journal of Advanced Robotic Systems, 2008, vol. 5, No. 2, pp. 177-184.
Pylatiuk et al., "Design and Evaluation of a Low-Cost Force Feedback System for Myoelectric Prosthetic Hands", 18 J. Prosthetics and Orthotics 57-61 (2006).
Pylatiuk et al., "Results of an Internet Survey of Myoelectric Prosthetic Hand Users", Prosthetics and Orthotics International, Dec. 2007, vol. 31, No. 4, pp. 362-370.
Ryew et al., "Robotic Finger Mechanism with New Anthropomorphic Metacarpal Joint", 26th Annual Conference of the IEEE Industrial Electronics Society, 2000. IECON 2000, vol. 1, pp. 416-421.
Schulz et al., "Die Entwicklung Einer Multifunktionalen Kosmetischen Handprothese", Prothetik, Orthopädie-Technik, Aug. 2006, pp. 627-632.
The Weir Thesis ("Weir Thesis") is entitled "An Externally-Powered, Myo-Electrically Controlled Synergetic Prosthetic Hand for the Partial-Hand Amputee", published Aug. 1989, pp. 365.
Touch Bionics PowerPoint Presentation in 3 pages, believed to be shown at ISPO Conference in Leipzig, Germany, May 2016. (Applicant requests that the Examiner consider this reference as qualifying as prior art as of the date indicated, but Applicant does not admit its status as prior art by submitting it here and reserves the right to challenge the reference's prior art status at a later date).
Touch Bionics PowerPoint Slide in 1 page, believed to be presented at Advanced Arm Dynamics company Jan. 11, 2016. (Applicant requests that the Examiner consider this reference as qualifying as prior art as of the date indicated, but Applicant does not admit its status as prior art by submitting it here and reserves the right to challenge the reference's prior art status at a later date).
Touch Bionics Screenshots of video in PowerPoint Presentation in 4 pages, believed to be shown at ISPO Conference in Leipzig, Germany, May 2016. (Applicant requests that the Examiner consider this reference as qualifying as prior art as of the date indicated, but Applicant does not admit its status as prior art by submitting it here and reserves the right to challenge the reference's prior art status at a later date).
Ward, Derek Kempton, "Design of a Two Degree of Freedom Robotic Finger", Sep. 1996, pp. 155.
Weir et al., "A Myoelectrically Controlled Prosthetic Hand for Transmetacarpal Amputations", JPO Journal of Prosthetics and Orthotics, Jun. 2001, vol. 13, No. 2, pp. 26-31.
Weir et al., "The Design and Development of a Synergetic Partial Hand Prosthesis with Powered Fingers", RESNA '89, Proceedings of the 12th Annual Conference, Technology for the Next Decade, Jun. 25-30, 1989, pp. 473-474.
"World's First Bionic Hand Factory Opened by Scottish Company", DailyMail.com, Jan. 8, 2008, https://www.dailymail.co.uk/sciencetech/article-506661/Worlds-bionic-hand-factory-opened-Scottish-company.html, pp. 4.

\* cited by examiner

SYSTEMS AND METHODS FOR CONTROLLING A PROSTHETIC HAND

CROSS-REFERENCE TO RELATED APPLICATIONS

This application is a continuation of U.S. patent application Ser. No. 15/307,385, filed on Oct. 28, 2016, entitled "Systems And Methods For Controlling A Prosthetic Hand," which claims priority benefit and is a National Stage Entry of International Patent Application No. PCT/GB2015/051356, filed on May 8, 2015, entitled "Systems And Methods For Controlling A Prosthetic Hand," which claims priority benefit to G.B. App. No. 1408253.1, filed May 9, 2014, entitled "Systems And Methods For Controlling A Prosthetic Hand," each of which is hereby incorporated herein by reference in its entirety.

FIELD OF THE INVENTION

The present invention is directed to the field of prosthetics, and more particularly prosthetic hands. Specifically, the present invention provides systems and methods for controlling a motorized prosthetic hand.

BACKGROUND OF THE INVENTION

Motorized prosthetic hands are known, in which one or more digits of the hand are each provided with an individual electric motor in order to manipulate the respective digits into desired positions and grips. Each drive motor may be controlled by means of switches which are actuated by known means such as residual digit movement or wrist movement. Alternatively or in addition, control of each digit motor may be by means of pressure sensitive resistors or signals derived from the electromyographic (EMG) activity of residual muscle actions. Whichever control method is used, repeated muscle actions or movements of the wrist or residual digits will result in fatigue and discomfort for the hand wearer after a relatively short period of time.

It is therefore an aim of the present invention to obviate or mitigate this disadvantage with existing systems and methods for controlling prosthetic hands.

SUMMARY OF THE INVENTION

According to a first aspect of the invention there is provided a method of controlling a prosthetic hand having at least one motorized component, the method comprising the steps of:
  providing the hand with a first wireless transceiver and a controller in communication with one another;
  storing at least one manipulation instruction relating to the at least one component;
  assigning a code relating to the at least one manipulation instruction to at least one second wireless transceiver;
  placing the at least one second transceiver in a location at which the at least one manipulation instruction is to be given; and
  the controller manipulating the at least one component in accordance with the at least one manipulation instruction when the first transceiver communicates to the controller that the at least one second transceiver is within a predetermined distance of the first transceiver.

The step of storing the at least one manipulation instruction may comprise:
  the wearer of the hand sending one or more control signals to the controller to manipulate the at least one component into a desired position; and
  storing the at least one manipulation instruction based upon the desired position of the component.

The manipulation of the at least one component in accordance with the manipulation instruction may only take place following an instruction signal sent from the wearer of the hand to the controller.

A plurality of manipulation instructions may be stored and respective codes are assigned to a corresponding plurality of second transceivers, each of the second transceivers is placed at a location at which its assigned manipulation instruction is to be given, and the controller manipulates the at least one component in accordance with the manipulation instruction assigned to a particular second transceiver when that particular second transceiver is within the predetermined distance of the first transceiver.

Alternatively, a pair of sequential manipulation instructions may be stored and a respective pair of codes are assigned to a pair of second transceivers, the pair of second transceivers are placed at locations at which the sequential manipulation instructions are to be given, and the controller manipulates the at least one component in accordance with a first manipulation instruction assigned to a first of the pair of second transceivers when that particular second transceiver is within the predetermined distance of the first transceiver, and the controller manipulates the at least one component in accordance with a second manipulation instruction assigned to a second of the pair of second transceivers when that particular second transceiver is within the predetermined distance of the first transceiver.

The first and second transceivers may be Bluetooth transceivers.

The first transceiver may search for the at least one second transceiver at predetermined time intervals of between 200 ms and 500 ms.

The predetermined distance between the first and second transceivers may be less than or equal to 18 cm.

According to a second aspect of the present invention there is provided a method of controlling a prosthetic hand having at least one motorized component, the method comprising the steps of:
  providing the hand with a first wireless transceiver and a controller in communication with one another;
  storing a plurality of manipulation instructions relating to the at least one component;
  assigning a code relating to a subset of the plurality of stored manipulation instructions to at least second wireless transceiver;
  placing the at least one second transceiver in a location at which the subset of manipulation instructions are desired; and
  the controller manipulating the at least one component in accordance with one of the subset of manipulation instructions when the first transceiver communicates to the controller that it is at the location, wherein the manipulation instruction executed by the controller is selected from the subset of instructions based upon a control signal from the wearer of the hand.

There may be one second transceiver, and the first transceiver communicates to the controller that it is at the location when the first transceiver is within a predetermined distance of the second transceiver.

The predetermined distance between the first and second transceivers may be less than or equal to 18 cm.

Alternatively, there may be three second transceivers which between them define the location, and the first transceiver communicates to the controller that is at the location when the position of the first transceiver is triangulated to the location by the second transceivers.

The first and second transceivers may be Bluetooth transceivers.

The first transceiver may search for the at least one second transceiver at predetermined time intervals of between 200 ms and 500 ms.

According to a third aspect of the invention there is provided a system for controlling a prosthetic hand having at least one motorized component, the system comprising:
   a first wireless transceiver located on the hand;
   a controller in communication with the first transceiver and the motorized component;
   an operator interface having at least one manipulation instruction stored thereon, and being in communication with the controller; and
   at least one second wireless transceiver which is assigned a code relating to the at least one manipulation instruction by the operator interface and is located in a location at which the at least one manipulation instruction is to be given;
   wherein the controller manipulates the at least one component in accordance with the at least one manipulation instruction when the first transceiver communicates to the controller that the at least one second transceiver is within a predetermined distance of the first transceiver.

The operator interface may store at least one manipulation instruction relating to a desired position of the component following the manipulation of the component into the desired position by the wearer of the hand.

The system may further comprise a plurality of second transceivers which are each assigned a code relating to a manipulation instruction by the operator interface and are each located in a location at which each respective manipulation instruction is to be given, and wherein the controller manipulates the at least one component in accordance with the manipulation instruction assigned to a particular second transceiver when that particular second transceiver is within the predetermined distance of the first transceiver.

The first and second transceivers may be Bluetooth transceivers.

The predetermined distance between the first and second transceivers may be less than or equal to 18 cm.

There may be three second transceivers which communicate with the operator interface such that the interface can triangulate the position of the first transceiver.

The operator interface may be a mobile application provided upon a mobile communications device.

BRIEF DESCRIPTION OF THE DRAWINGS

A preferred embodiment of the present invention will now be described, by way of example only, with reference to the accompanying drawings in which.

DETAILED DESCRIPTION OF THE DRAWINGS

Figure 1:
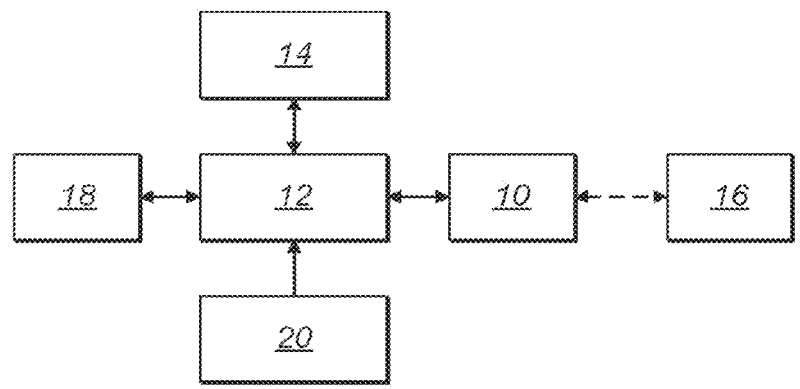
FIG. 1 is a schematic diagram showing a system for controlling a prosthetic hand having at least one motorized component.

FIG. 1 schematically illustrates the components of a system for controlling a prosthetic hand having at least one motorized component. The motorized component(s) of the hand may be one or more digits, or a rotatable wrist component, for example. The system comprises a first transceiver 10 and an electronic controller 12 which is in two-way communication with the first transceiver 10. The controller 12 is also in two-way communication with an electric motor 14 which drives the motorized component when an appropriate signal is received from the controller 12. The system also comprises at least one second transceiver, referred to from now on as a locator, 16 which can wirelessly communicate with the first transceiver 10. The first and second transceivers 10, 16 may be Radio Frequency Identification (RFID) transceivers, but are preferably Bluetooth transceivers and most preferably Bluetooth Low Energy (BLE) transceivers.

The system further comprises an operator interface 18 which is in wireless communication with the first transceiver 10 and hence the controller 12. The operator interface 18 may be a personal computer running a control and set up program for the system, but is preferably a mobile communications device such as a smart phone or tablet which is running a mobile application through which the user sets up and controls the system. The operator interface preferably communicates with the first transceiver via Bluetooth.

Optionally, the system may also comprise one or more input devices 20 which can communicate control signals to the controller 12 in response to inputs from the wearer of the hand. The input device(s) 20 may be switches which are actuated by known means such as residual digit movement or wrist movement. Alternatively or in addition, the input device(s) 20 may be pressure sensitive resistors or other sensors which derive signals from the electromyographic (EMG) activity of the wearer's residual muscle actions.

The hand uses a known drive arrangement in order to manipulate the motorized component(s). An example of one such arrangement which is suited to the purpose is that disclosed in the same applicant's earlier publication WO2007/063266. Further description of the specific drive arrangement will therefore not be provided herein.

Figure 2:
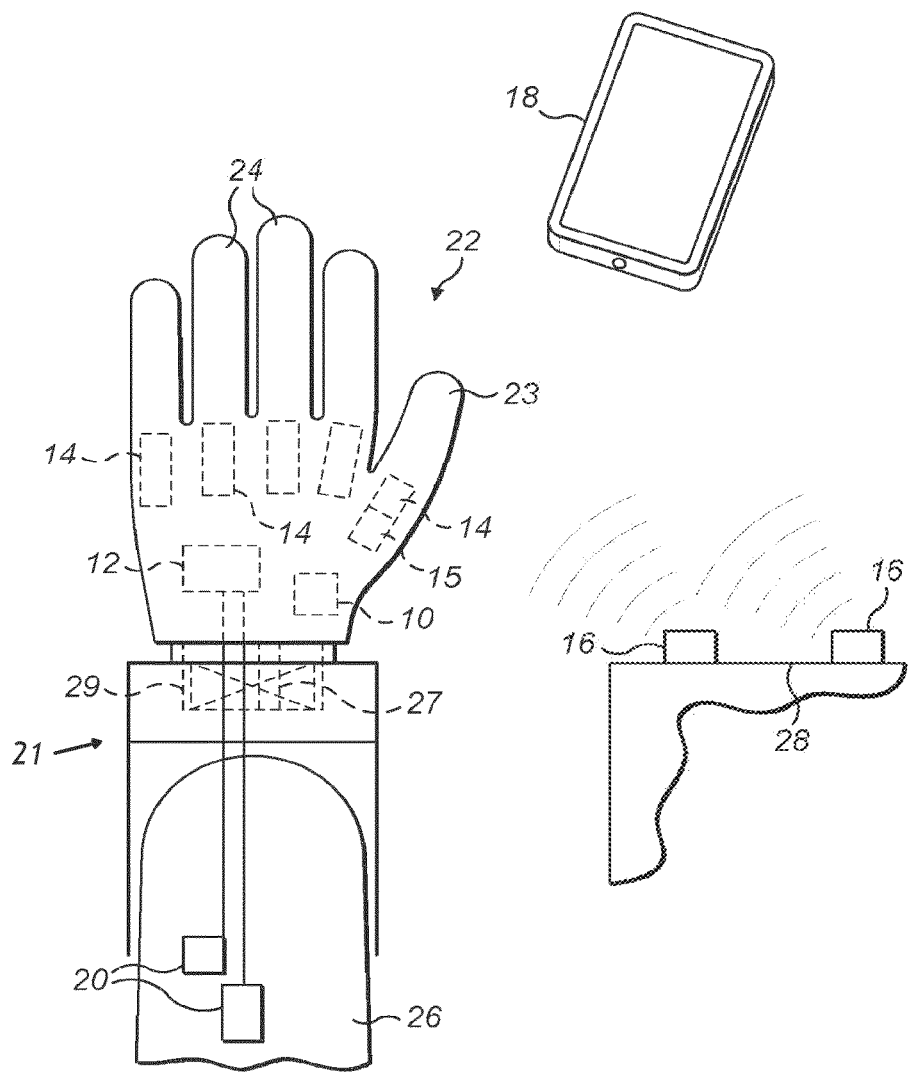
FIG. 2 illustrates the system of FIG. 1 in operation.

FIG. 2 illustrates the various components of the system when in operational use. Detailed description of the operational procedures employed by the system will be set out below, but FIG. 2 shows a prosthetic hand 22 which comprises a motor 14 for each of the four finger digits 24 on the hand. The hand 22 also has a thumb digit 23 which has a first motor 14 to pivot the thumb in the same manner as the fingers, and a second motor 15 for rotational movement of the thumb. Also located on the hand 22 are the first transceiver 10 and the controller 12, and in the illustrated embodiment the controller is also connected to a pair of input devices 20 in the form of EMG sensors located upon the muscles in the wearer's forearm 26.

The hand 22 is mounted on a base 21 which is attached to the stump of the forearm 26. The hand 22 may be provided with a first wrist motor 27 which rotates the hand relative to the base 21, and/or a second wrist motor 29 which pivots the hand relative to the base 21. Where present, the or each wrist motor 27,29 is connected to the controller 12 so that the controller 12 can control the motor 27,29 in the same manner as it controls the digit motors 14,15.

A mobile communications device in the form of a smart phone provides the operator interface 18. At least one locator 16 is located upon a surface 28 so as to identify a given location to the first transceiver 10. In the illustrated embodiment of FIG. 2 there are a pair of locators 16, which are intended to provide sequential and separate identification of their respective locations to the first transceiver. Further details on how the system employs the location information from the, or each, locator will be set out below.

Figure 3:
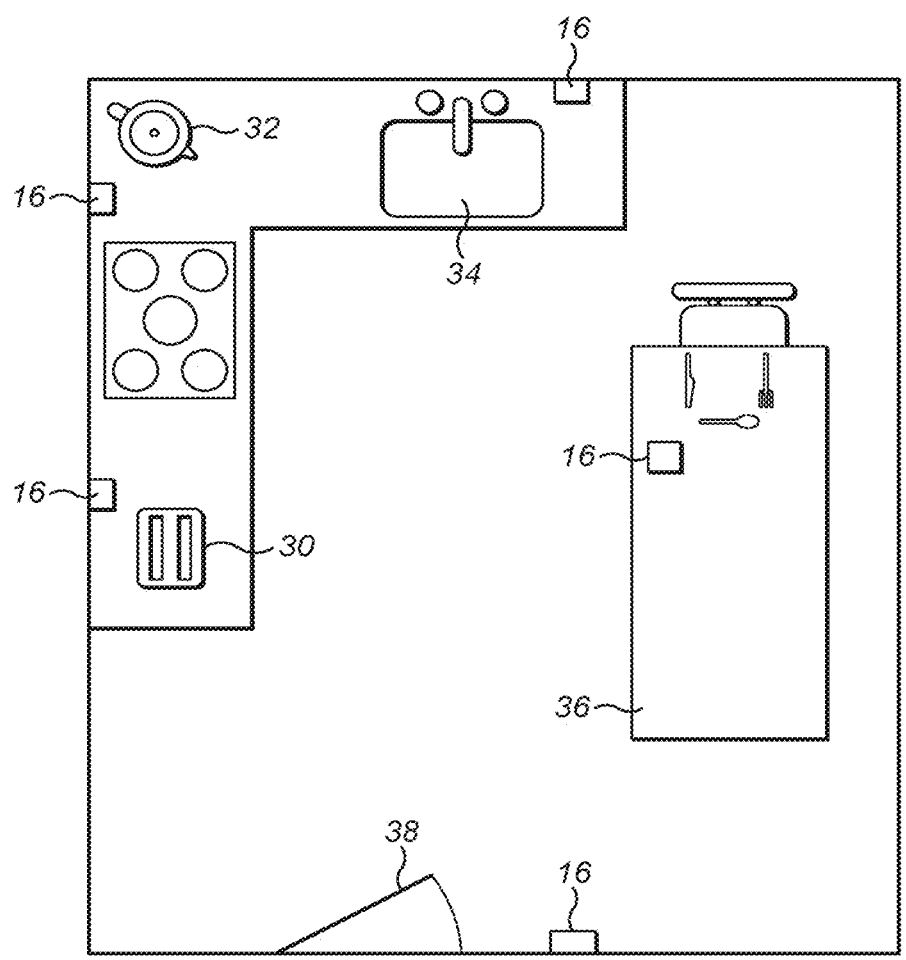
FIG. 3 illustrates how a number of transceivers from the system of FIGS. 1 and 2 may be located within a room.

FIG. 3 provides an example of how a plurality of locators may be placed in a space or room, in order to identify various locations. In the illustrated example, the room is a kitchen and locators 16 have been located proximate a toaster 30, a kettle 32 and the taps of the kitchen sink 34, as well as on the kitchen table 36 and a wall adjacent the entrance door 38 into the kitchen. As will be explained further below, the purpose of locating locators 16 at selected locations is that it allows the system to switch the components of the prosthetic hand of a wearer between various predetermined positions to form specific grips or the like for when the wearer wishes to turn on the taps or hold cutlery to eat a meal, for example. The wearer brings the hand, and first transceiver, within a predetermined distance of a locator with the result that the components of the hand take on a specific position related to that particular location, as identified by the locator.

Alternatively, or in addition, one or more of the locators 16 located in the space may be provided in order to establish when the wearer has entered the space rather than to automatically instruct the hand to form a specific grip. For example, in the kitchen shown in FIG. 3 the locator by the entrance door 38 may be provided simply to inform the first transceiver and controller on the hand when the hand has entered the kitchen space. The benefit of this particular arrangement will be set out in more detail below.

Figure 4:
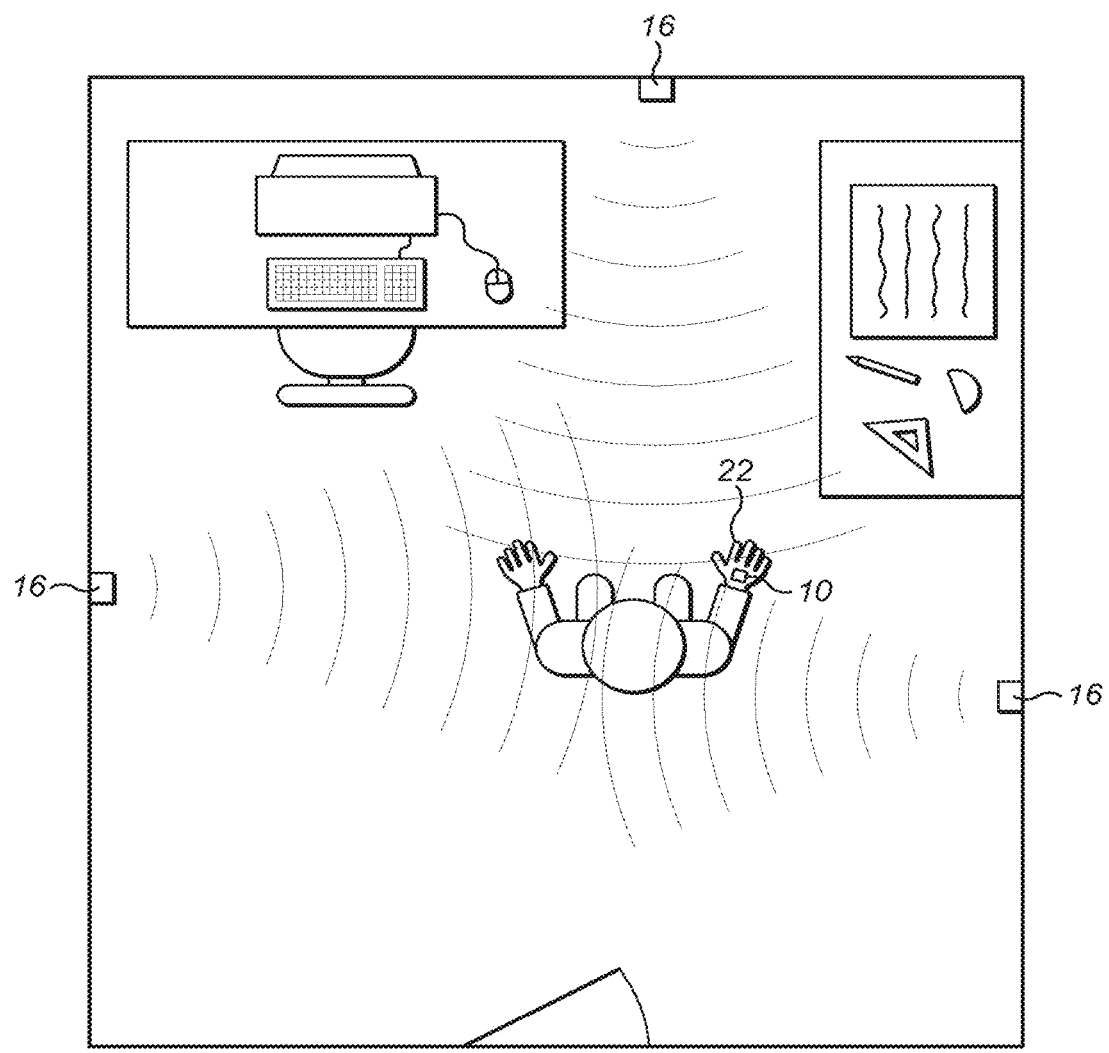
FIG. 4 illustrates how the location of the wearer of the prosthetic hand may be established using a number of transceivers.

FIG. 4 shows a further arrangement of locators 16 which may be employed to determine when the wearer is in a given location. In this arrangement there are three locators provided, each on a different wall of an office space. By placing the three transceivers 16 in this arrangement it is possible for the position of the first transceiver 10 and hand 22 to be triangulated as an alternative to the single locator located adjacent the door in FIG. 3.

Figure 5:
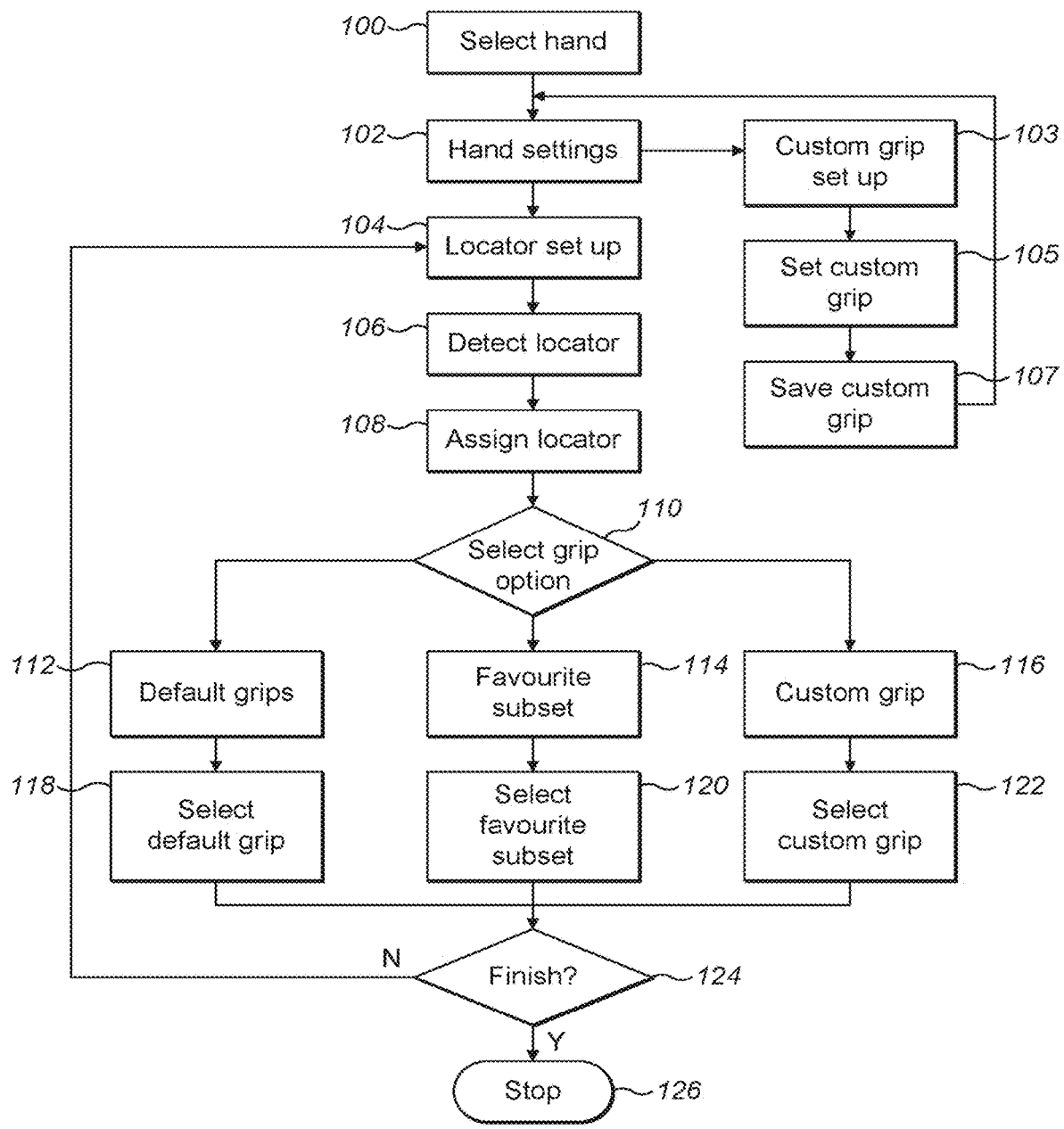
FIG. 5 is a flow chart showing a procedure for setting up the system.

FIG. 5 shows a flow chart of how the system is initially set up using the operator interface. As described above, this is preferably done via a mobile application running on a smart phone or tablet but may alternatively be done via a program on a personal computer. The mobile application is launched in the smart phone or tablet and the user is then asked to select the prosthetic hand for which the setup is being performed at step 100. Typically, this is done by the first transceiver located in the hand transmitting data to the smart phone and allowing the user to identify their prosthetic hand or hands. Once the hand is identified the settings menu for that hand is accessed at step 102. Within the settings menu is a "locator set up" option which is then accessed at step 104. At this point the locator, otherwise known as the locator, is activated so that it may be detected by the smart phone at step 106. Once detected, the detected locator is selected at step 108 so that it may then be assigned an identifier code corresponding with a manipulation instruction for one or more of the motorized components of the hand to move into a given position or grip.

The assignation of the identifier code begins with the operator choosing a particular grip option at step 110. In the illustrated example there are three grip options offered, but the invention is not limited to the specific options listed herein. Instead, there may be at least one grip option provided at step 110. From the three options in the illustrated example, the user can selected from a group of default grips and positions for the components via step 112, a "favorite" subset of the default grips at step 114, or a custom grip created and saved by the user at step 116.

When saving a custom grip, the user accesses a custom grip set up 103 via the settings step 102. From the set up step 103 the user selects a step 105 to set a custom grip. At this point the user manipulates the one or more components of the hand into a desired position using the normal manner in which they control the hand, such as via the control switches or sensors referred to above. The controller receives data back from the or each component motor regarding the run time it took for the motor to put the component in the position desired by the user. The controller then sends this data to the operator interface via the first transceiver so that the positional information may be saved at step 107 in the application as a custom grip. Then, whenever the user wishes to assign a code relating to that saved custom grip to a locator they do so via step 116 of the set up procedure.

Once the user has indicated which grip option they wish to access for the locator being set up, they then select a specific grip or grip subset via the respective selection steps 118,120,122. An identifier code for that specific grip or subset is then assigned and transmitted to the locator. Finally, the set up will ask the user at step 124 if they have finished setting up locators with grip codes. If so, the set up program will terminate at step 126. If not, it returns to locator set up step 104.

Figure 6:
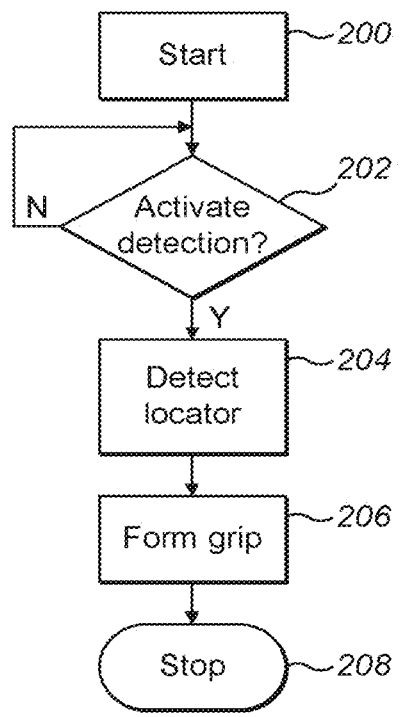
FIG. 6 is a flow chart showing operating procedures for the system when in first and second operating modes.

FIG. 6 illustrates the procedural steps used by the system uses to control the hand when in the presence of the system shown in either FIG. 2 or FIG. 3 for example. After starting the process at step 200 the process will check at step 202 for a signal that the wearer of the hand is wanting to switch the system in a detection mode. In the detection mode the various locators which have been set up using the process shown in FIG. 5 will become visible to the first transceiver. There are a number of ways in which the wearer can activate the detection mode, but one example is to hold an EMG signal via a forearm muscle for a particular time period, say between 0.5 and 1.5 seconds. An alternative is to hold the hand in the open position for the same time period. When such a signal is detected at step 202 the first transceiver will start actively searching at step 204 for locators which are active and have been assigned a manipulation code, as described above. The first transceiver is typically set up to search for locators every 200-500 ms. When the first transceiver detects a locator it signals the controller and at step 206 the controller signals the motor of at least one motorized component to move the component into the position dictated by the saved manipulation instruction whose code has been assigned to the detected locator. The system is preferably set up so that the first transceiver detects a locator when it comes within 18 cm of the locator. The process then terminates at step 208 or may repeat.

The process of FIG. 6 applies where one or more locators are present which have been assigned codes which relate to default grips or custom grips. One practical embodiment of this arrangement can be seen in FIG. 3, which as described above shows a kitchen environment. Each of the locators, or locators, 16 positioned in the kitchen has been assigned a code which relates to a manipulation instruction and a default or custom grip which is desired at the point at which the locator 16 is going to be placed. This may be a particular grip to hold and pour the kettle 32, which may be a different grip to that required to turn on a tap at the sink 34 or hold a knife or fork when eating at the kitchen table 36. Following the process shown in FIG. 6, the hand wearer would enter the kitchen and then give the activation signal which instructs the first transceiver to start searching for active locators. This then means that whenever the wearer brings the hand and first transceiver within 18 cm of a locator the grip whose code is assigned to that locator will be automatically formed by the hand under the instructions of the controller.

Figure 7:
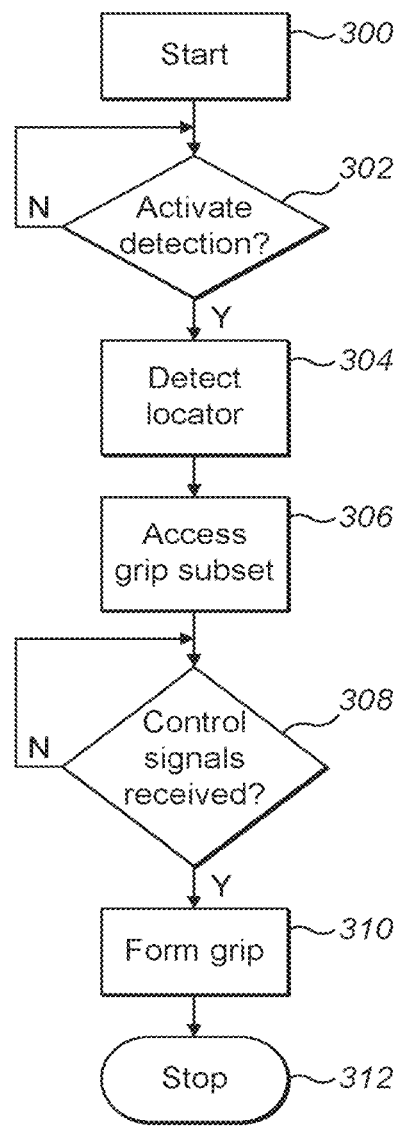
FIG. 7 is a flow chart showing operating procedures for the system when in a third operating mode.

An alternative process is shown in FIG. 7 which is for use where a locator has been assigned a code relating to a particular subset of grips rather than a specific grip. This process would therefore be used in the example described above where the kitchen of FIG. 3 has a single locator on the wall adjacent the door 38 rather than a number of locators around the room. As already described with respect to FIG. 5, when setting up this arrangement the locator is assigned a code which relates to a chosen subset of the default or custom grips, preferably 4-6 grips which are all likely to be required in a particular environment such as, for example, a kitchen, an office space or when driving in a vehicle. These subsets of grips would be accessed through a "favorites" menu in the mobile application or program.

This alternative process starts at step 300 and its initial steps are identical to those of the process shown in FIG. 6. Step 302 searches for an activation signal from the wearer of the hand, which is again preferably a held EMG signal lasting between 0.5 and 1.5 seconds. Once the activation signal is given the first transceiver begins looking for active locators at step 304. As before the first transceiver is looking for a locator every 200 to 500 ms, and will find a locator when it comes within around 18 cm of it. When the locator is detected the first transceiver informs the controller and the controller then has access at step 306 to only the 4-6 grips whose codes have been assigned to the detected locator.

Unlike with the previous process, the hand does not automatically form grips when employing this alternative process. Instead, the purpose of this process is to still give control of the hand to the wearer, but to reduce the number of grips available from perhaps 30 down to 4-6 which relate to the particular environment which the wearer has entered. Thus at step 308, the process awaits one or more control signals from the wearer to then form at step 310 one of the subset of grips which is selected based upon that signal or signals. The process then stops at step 312 or may loop back to step 304 or 308 as desired.

A modification to the aforementioned process is to use the triangulation arrangement shown in FIG. 4 to very accurately detect the location of the hand and wearer without the hand having to go within a predetermined distance of a locator. The difference being that at step 304 the first transceiver would not be searching for a single locator but would be instead be communicating with all three locators in order to establish when the first transceiver has entered the location covered by the locators. Then the process would proceed to step 306 and access the grip subset as described above.

The present invention provides systems and processes for controlling a prosthetic hand having at least one motorized component, in which repeated muscle actions or movements of the wrist or residual digits by the wearer are not required to control the hand, or are at least very much reduced. Thus, the present invention reduces fatigue and discomfort for the hand wearer caused by frequently having to form grips or manipulate the hand. The present invention can be set up so that the hand automatically forms a given grip or position when placed at a certain location, or else the hand only has access to a small subset of grips when in that location. The former removes the need for the wearer to control the hand at all, whilst the latter significantly reduces the amount of actions or signals which need to be produced by the wearer.

When in the set up process for assigning a manipulation code to a locator, when the locator to which the code is being assigned is detected the mobile application or program may indicate via the operator interface the remaining battery life of that locator.

The triangulation system shown in FIG. 4 will have at least three locators, or locators, but may have more than three.

The operation process shown in FIG. 6 may have a safety step whereby the hand wearer must provide an activation signal 202 before every grip change, rather than the preferred arrangement in which the grip will change as soon as the first transceiver comes within the predetermined distance of a locator. That way there are no unexpected grip changes of the hand if the wearer accidentally puts the hand within the predetermined distance of an alternative locator. However, this safety step is not essential and can be disabled. For example, a pair of locators may be placed either side of a wearer who works on an assembly or production line. Here one locator may be assigned a code to open the hand and release an item and the other assigned a code for closing the hand and picking up an item, for example. That way the grips will change automatically whenever the worker places the hand near the related locator without having to give the activation signal every time they wish the grip to change, which would not be practical in such an activity.

As seen in FIG. 2, a pair of locators may also be set up so that each is assigned a code which relates to one half of a desired hand manipulation. For example, a first locator could be assigned a code to rotate the wrist of a prosthetic hand as the hand passes the locator, and a second locator could be assigned a code for opening or closing the hand. In this way, the system could provide the hand with an automatic sequence of movements as the wearer sweeps the hand over the pair of locators. Such a set up could save time for the wearer is the desired actions are to be repeated numerous times. The system may employ more than two locators set up to provide a sequence of instruction codes to the first transceiver.

The "favorites" process illustrated in FIG. 7 may include an additional step of indicating to the wearer that the hand is now operating in the favorites mode with the reduced subset of grips available. This indicator may be a brief twitch of all of the digits on the hand, an audible beep, or one or more flashes of an LED upon the locator.

Although the preferred distance at which the first transceiver will detect a locator is 18 cm or less, it can be adjusted to suit individual situations and applications. For example, in the favorite's mode it may be sufficient for the first and locators to come within 30 cm of one another. Where Bluetooth is used for the wirelessly communicating first and locators, the predetermined activation distance can be adjusted as required via the mobile application or control program.

The mobile application or program running the process and system may be set up so that the user can review what code is assigned to a given locator, in case the user has forgotten after the locator was set up.

The locators may be set up so that they record data each time the first transceiver comes within the predetermined distance of the locator. That data may then be uploaded to the operator interface for analysis by an occupational therapist, for example.

These and other modifications and improvements may be incorporated without departing from the scope of the present invention.

What is claimed is:

1. A prosthetic hand comprising:
    at least one motorized component;
    one or more processors;
    a memory storing a plurality of first manipulation instructions associated with a plurality of control signals, wherein based at least in part on receipt of a particular control signal of the plurality of control signals, the one or more processors are configured to instruct the at least one motorized component to move in accordance with a particular first manipulation instruction of the plurality of first manipulation instructions to cause a prosthetic hand to form a particular grip of a first plurality of hand grips; and
    a first wireless transceiver configured to receive an activation signal indicative of a plurality of second manipulation instructions from a second wireless transceiver;
    wherein the one or more processors are configured to:
        based at least in part on the activation signal, associate the plurality of second manipulation instructions with the plurality of control signals,
        wherein following association of the plurality of second manipulation instructions with the plurality of control signals and based at least in part on receipt of the particular control signal, the one or more processors are configured to instruct the at least one motorized component to move in accordance with a particular second manipulation instruction of the plurality of second manipulation instructions to cause the prosthetic hand to form a particular grip of a second plurality of hand grips, wherein the second plurality of hand grips is different from the first plurality of hand grips.

2. The prosthetic hand of claim 1, wherein the at least one motorized component comprises at least one of a thumb digit or one or more finger digits, wherein the one or more finger digits are different from the thumb digit.

3. The prosthetic hand of claim 1, wherein the second wireless transceiver transmits the activation signal based at least in part on a determination that the first wireless transceiver is within a threshold distance from the second wireless transceiver.

4. The prosthetic hand of claim 1, wherein the one or more processors are further configured to receive the particular control signal from a myoelectric electrode, wherein the particular control signal is based at least in part on a myoelectric signal received at the one or more myoelectric electrodes from a muscle of a wearer of the prosthetic hand.

5. The prosthetic hand of claim 1, wherein the one or more processors are further configured to:
    detect an input signal from a myoelectric electrode, wherein the input signal is based at least in part on a myoelectric signal received at the myoelectric electrode from a muscle of a wearer of the prosthetic hand; and
    activate a detection mode of a first transceiver based at least on part on detection of the input signal, wherein the detection mode of the first wireless transceiver allows the first wireless transceiver to receive signals from one or more other transceivers including the second wireless transceiver.

6. The prosthetic hand of claim 5, wherein to activate the detection mode of the first transceiver, the one or more processors are further configured to change a state of the first transceiver from an inactive detection mode state to an active detection mode state, wherein the inactive detection mode state prevents the first wireless transceiver from receiving the activation signal from the second wireless transceiver.

7. The prosthetic hand of claim 1, wherein the one or more processors are further configured to:
    detect an input signal from a myoelectric electrode; and
    based at least in part on the input signal, manipulate the at least one motorized component in accordance with a particular second manipulation instruction of the plurality of second manipulation instructions such that the prosthetic hand forms the particular grip of the plurality of second grips, wherein the one or more processors are configured such that it does not manipulate the at least one motorized component in accordance with the at least one second manipulation instruction until the input signal is detected.

8. A system for adjusting instructions of a prosthetic hand, the system comprising:
    at least one motorized component;
    one or more processors;
    a memory storing a plurality of first manipulation instructions associated with a plurality of control signals, wherein based at least in part on receipt of a particular control signal of the plurality of control signals, the one or more processors are configured to instruct the at least one motorized component to move in accordance with a particular first manipulation instruction of the plurality of first manipulation instructions to cause a prosthetic hand to form a particular grip of a first plurality of hand grips; and
    a first wireless transceiver configured to receive an activation signal indicative of a plurality of second manipulation instructions from a second wireless transceiver;
    wherein the one or more processors are configured to:
        based at least in part on the activation signal, associate the plurality of second manipulation instructions with the plurality of control signals,
        wherein following association of the plurality of second manipulation instructions with the plurality of control signals and based at least in part on receipt of the particular control signal, the one or more processors are configured to instruct the at least one motorized component to move in accordance with a particular second manipulation instruction of the plurality of second manipulation instructions to cause the prosthetic hand to form a particular grip of a second plurality of hand grips, wherein the second plurality of hand grips is different from the first plurality of hand grips.

9. The system of claim 8, wherein the at least one motorized component comprises at least one of a thumb digit or one or more finger digits, wherein the one or more finger digits are different from the thumb digit.

10. The system of claim 8, wherein the first wireless transceiver transmits the activation signal based at least in part on a determination that the second wireless transceiver is within a threshold distance from the first wireless transceiver.

11. The system of claim 8, wherein the one or more processors are further configured to receive a particular control signal of the plurality of control signals from a myoelectric electrode, wherein the particular control signal is based at least in part on a myoelectric signal received at the myoelectric electrode from a muscle of a wearer of the prosthetic hand.

12. The system hand of claim 8, wherein the one or more processors are further configured to:
- detect an input signal from a myoelectric electrode, wherein the input signal is based at least in part on a myoelectric signal received at the myoelectric electrode from a muscle of a wearer of the prosthetic hand; and
- activate a detection mode of the second transceiver based at least on part on the detection of the input signal, wherein the detection mode of the second wireless transceiver allows the second wireless transceiver to receive signals from one or more other transceivers including the first wireless transceiver.

\* \* \* \* \*

UNITED STATES PATENT AND TRADEMARK OFFICE
CERTIFICATE OF CORRECTION

| | |
|---|---|
| PATENT NO. | : 11,234,842 B2 |
| APPLICATION NO. | : 16/249696 |
| DATED | : February 1, 2022 |
| INVENTOR(S) | : Hugh Gill |

It is certified that error appears in the above-identified patent and that said Letters Patent is hereby corrected as shown below:

On the Title Page

Page 4, Column 1 (Other Publications), Line 1, delete "Anthromorphic" and insert -- Anthropomorphic --.

Page 4, Column 1 (Other Publications), Line 14, delete "or" and insert -- of --.

Page 5, Column 2 (Other Publications), Line 9, delete "Frederiction," and insert -- Fredericton, --.

Page 5, Column 2 (Other Publications), Line 21, delete "blonics-" and insert -- bionics- --.

Signed and Sealed this
Twentieth Day of September, 2022

*Katherine Kelly Vidal*

Katherine Kelly Vidal
*Director of the United States Patent and Trademark Office*